(12) United States Patent
Bonnette et al.

(10) Patent No.: US 6,932,828 B2
(45) Date of Patent: Aug. 23, 2005

(54) GUIDEWIRE OCCLUSION SYSTEM UTILIZING REPEATABLY INFLATABLE GAS-FILLED OCCLUSIVE DEVICE

(75) Inventors: Michael J. Bonnette, Minneapolis, MN (US); Eric J. Thor, Arden Hills, MN (US)

(73) Assignee: Possis Medical, Inc., Minneapolis, MN (US)

( * ) Notice: Subject to any disclaimer, the term of this patent is extended or adjusted under 35 U.S.C. 154(b) by 188 days.

(21) Appl. No.: 10/012,903

(22) Filed: Nov. 6, 2001

(65) Prior Publication Data

US 2003/0088263 A1 May 8, 2003

(51) Int. Cl.$^7$ ............................................. A61M 25/10
(52) U.S. Cl. ....................... 606/194; 606/191; 606/195; 604/96.01; 604/99.01
(58) Field of Search .................................. 606/191–200, 606/168; 604/96.01–103

(56) References Cited

U.S. PATENT DOCUMENTS

| | | | |
|---|---|---|---|
| 4,332,254 A | * | 6/1982 | Lundquist .................... 606/194 |
| 4,573,470 A | | 3/1986 | Samson et al. |
| 4,573,966 A | | 3/1986 | Weikl et al. |
| 4,636,195 A | | 1/1987 | Wolinsky |
| 4,646,719 A | | 3/1987 | Neuman et al. |
| 4,651,738 A | * | 3/1987 | Demer et al. ................ 604/194 |
| 4,733,652 A | | 3/1988 | Kantrowitz et al. |
| 4,838,268 A | | 6/1989 | Keith et al. |
| 4,865,587 A | | 9/1989 | Walling |
| 5,059,176 A | | 10/1991 | Winters |
| 5,059,178 A | | 10/1991 | Ya |
| 5,106,363 A | * | 4/1992 | Nobuyoshi ................. 604/6.11 |
| 5,135,482 A | | 8/1992 | Neracher |
| 5,167,239 A | | 12/1992 | Cohen et al. |
| 5,171,221 A | | 12/1992 | Samson |
| 5,195,955 A | | 3/1993 | Don Michael |
| 5,209,727 A | | 5/1993 | Radisch, Jr. et al. |
| 5,320,604 A | | 6/1994 | Walker et al. |
| 5,324,260 A | * | 6/1994 | O'Neill et al. .......... 604/103.08 |
| 5,334,153 A | * | 8/1994 | McIntyre et al. ........ 604/99.02 |
| 5,380,284 A | | 1/1995 | Don Michael |
| 5,520,645 A | | 5/1996 | Imran et al. |
| 5,688,234 A | | 11/1997 | Frisbie |
| 5,713,917 A | | 2/1998 | Leonhardt et al. |
| 5,775,327 A | | 7/1998 | Randolph et al. |
| 5,776,100 A | | 7/1998 | Forman |
| 5,779,688 A | | 7/1998 | Imran et al. |
| 5,792,179 A | | 8/1998 | Sideris |
| 5,807,330 A | | 9/1998 | Teitelbaum |
| 5,827,324 A | | 10/1998 | Cassell et al. |

(Continued)

Primary Examiner—Julian W. Woo
Assistant Examiner—Sarah Webb
(74) Attorney, Agent, or Firm—Hugh D. Jaeger

(57) ABSTRACT

A guidewire occlusion system for use in vascular procedures includes a repeatably inflatable gas-filled occlusive device proximate a distal end of a tubular guidewire assembly having an extended sealable section proximate a proximal end. A gas inflation/evacuation system is removably connectable to the proximal end of the guidewire assembly and includes an evacuation system to evacuate air from the guidewire and an inflation system for introducing a gas under pressure into the guidewire to inflate the occlusive balloon a plurality of times. A sealing system is also removably connectable to the proximal end of the guidewire assembly and selectively seals the extended sealable section at one of a plurality of separate locations along the extended sealable section to form an airtight seal of the tubular guidewire. Each time a deflation of the occlusive device is desired to reestablish blood flow to the vessel downstream of the occlusive device, the extended sealable section is opened distal to the location of the last seal to quickly deflate the occlusive device.

33 Claims, 13 Drawing Sheets

U.S. PATENT DOCUMENTS

| | | | |
|---|---|---|---|
| 5,833,644 A | 11/1998 | Zadno-Azizi et al. | |
| 5,833,650 A | 11/1998 | Imran | |
| 5,843,022 A | 12/1998 | Willard et al. | |
| 5,865,721 A | 2/1999 | Andrews et al. | |
| 5,882,334 A * | 3/1999 | Sepetka et al. | 604/164.08 |
| 5,908,405 A | 6/1999 | Imran et al. | |
| 5,925,016 A | 7/1999 | Chornenky et al. | |
| 5,938,672 A | 8/1999 | Nash | |
| 5,980,486 A * | 11/1999 | Enger | 604/103.04 |
| 5,997,558 A | 12/1999 | Nash | |
| 6,021,340 A | 2/2000 | Randolph et al. | |
| 6,022,336 A | 2/2000 | Zadno-Azizi et al. | |
| 6,050,972 A | 4/2000 | Zadno-Azizi et al. | |
| 6,080,170 A | 6/2000 | Nash et al. | |
| 6,123,698 A * | 9/2000 | Spears et al. | 604/523 |
| 6,135,991 A | 10/2000 | Muni et al. | |
| 6,146,372 A | 11/2000 | Leschinsky et al. | |
| 6,159,195 A | 12/2000 | Ha et al. | |
| 6,171,328 B1 | 1/2001 | Addis | |
| 6,176,844 B1 | 1/2001 | Lee | |
| 6,203,561 B1 | 3/2001 | Ramee et al. | |
| 6,217,567 B1 | 4/2001 | Zadno-Azizi et al. | |
| 6,231,588 B1 | 5/2001 | Zadno-Azizi | |
| 6,241,706 B1 | 6/2001 | Leschinsky et al. | |
| 6,245,008 B1 | 6/2001 | Leschinsky et al. | |
| 6,245,089 B1 | 6/2001 | Daniel et al. | |
| 6,248,121 B1 | 6/2001 | Nobles | |
| 6,251,093 B1 * | 6/2001 | Valley et al. | 604/97.03 |
| 6,558,502 B2 * | 5/2003 | Divino et al. | 156/294 |
| 2001/0014821 A1 * | 8/2001 | Juman et al. | 623/1.11 |
| 2001/0051784 A1 * | 12/2001 | Brisken et al. | 604/22 |
| 2002/0042625 A1 * | 4/2002 | Stack et al. | 606/194 |

* cited by examiner

GUIDEWIRE OCCLUSION SYSTEM UTILIZING REPEATABLY INFLATABLE GAS-FILLED OCCLUSIVE DEVICE

RELATED APPLICATIONS

The present invention is related to two co-pending applications that are commonly assigned to the assignee of the present invention and filed concurrently herewith, the first of which is entitled "Guidewire Assembly Having Occlusive Device and Repeatably Crimpable Proximal End," application Ser. No. 10/012,891, and the second of which is entitled "Gas Inflation/Evacuation System and Sealing System for Guidewire Assembly Having Occlusive Device," application Ser. No. 10/007,788, a copy of each of which is attached and the disclosures of both of which are incorporated by reference.

FIELD OF THE INVENTION

The present invention relates generally to the field of vascular medical devices. More specifically, the present invention relates to a guidewire occlusion system for use in vascular procedures that uses a repeatably inflatable gas-filled occlusive device.

BACKGROUND OF THE INVENTION

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of non-surgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320,604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically-expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long, straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard non-surgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520,645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons as well as most guidewire occlusive balloons utilize a liquid fluid such as saline or saline mixed with a radiopaque marker for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high-pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternate embodiments in U.S. Pat. No. 6,217,567. The only suggestion for how the guidewire of the alternate embodiment is sealed is a valve type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid filled occlusive balloons can remain in place too long and take too long to deflate, increasing the risk of damages downstream of the occlusion. Occlusive filters are designed to address this problem, but suffer from blockage problems and can be complicated to deploy and retrieve and may allow small embolic particles to migrate downstream. Existing gas-filled occlusive balloons solve some of the problems of liquid filled occlusive balloons, but typically have utilized complicated valve and connection arrangements. It would be desirable to provide for an occlusive device that was effective, simple, quick to deploy and deflate, and that could overcome the limitations of the existing approaches.

SUMMARY OF THE INVENTION

The present invention is a guidewire occlusion system for use in vascular procedures that includes a repeatably inflatable gas-filled occlusive balloon or other occlusive device proximate a distal end of a tubular guidewire assembly having an extended sealable section at a proximal end. A gas inflation/evacuation system is removably connectable to the proximal end of the tubular guidewire assembly and includes an evacuation syringe to evacuate the tubular guidewire assembly and an inflation syringe or syringes for introducing a gas under pressure into the tubular guidewire assembly to inflate the occlusive balloon or other occlusive device a plurality of times. A sealing system is also removably connectible to the proximal end of the tubular guidewire assembly and selectively seals the tubular guidewire assembly at one of a plurality of separate locations along the extended sealable section to form an airtight seal of the tubular guidewire assembly. Each time a deflation of the occlusive balloon is desired in order to reestablish blood flow to the vessel downstream of the occlusive balloon, the proximal end of the extended sealable section preferably is cut distal to the location of the last seal to quickly deflate the occlusive balloon.

The advantage of the guidewire occlusion system of the present invention is that the occlusive device can be repeatably inflated and deflated a plurality of times during a vascular procedure in between which the proximal end of the tubular guidewire assembly is free of mechanical connections and obstructions and, therefore, the tubular guidewire assembly can function as a conventional exchange guidewire assembly for one or more over-the-wire catheters. Alternatively, the tubular guidewire assembly of the present invention can be shorter in length for use with rapid exchange catheter systems. Unlike operation of existing liquid filled occlusive devices, the present invention enables repeated and quick inflation and deflation which allows an operator to deploy the gas-filled occlusive device numerous times during a procedure for shorter periods of time, thereby reducing the risk of potential damage to downstream tissue. Unlike operation of other gas-filled occlusive devices, the simplicity of the present invention permits the tubular guidewire assembly to be used as a conventional exchange guidewire assembly. There are no complicated mechanical arrangements or valve systems internal to the tubular guidewire assembly that increase the cost, complexity, and potential for failure of the system.

In a preferred embodiment, the extended sealable section is an extended crimpable section and the sealing system includes a crimping mechanism. The extended crimpable section has a sufficient length to permit a plurality of crimps and cuts along the extended crimpable section and preferably has an outer diameter that is smaller than the outer diameter of the main body portion of the guidewire assembly. The crimping mechanism is used to crimp the extended crimpable section of the guidewire assembly to seal the guidewire assembly a plurality of times. Preferably, the gas inflation/evacuation system and the crimping mechanism and sealing mechanism of the sealing system constitute a handheld apparatus. Each time a deflation of the occlusive device is desired in order to reestablish blood flow to the vessel downstream of the occlusive device, the extended crimpable section is cut distal to the location of the last crimp so as to quickly deflate the occlusive device. Preferably, the extended crimpable section of the guidewire assembly is dimensioned and the crimping mechanism is arranged such that an effective outer diameter of the extended crimpable section at the location of a seal is no greater than the outer diameter of the main body portion of the guidewire assembly when the extended crimpable section is sealed.

In an alternate embodiment, the sealing mechanism is a plugging mechanism that selectively inserts a plug of material into the proximal end of the extended sealable section while maintaining an airtight seal between the guidewire assembly and the gas inflation/evacuation system. In one embodiment, the plug of material includes a wax/gel material and the sealing system includes wiping structure to remove excess wax/gel material from the outside of the extended sealable section once the wax/gel material has been inserted. In this embodiment, the extended sealable section may be opened either by cutting the extended sealable section distal to the location of the seal or by heating the proximal end of the extended sealable section.

In one embodiment for coronary vascular procedures, the guidewire assembly preferably has an effective length of at least 40 cm and more preferably at least 100 cm and an outer diameter of less than 0.060 inch and more preferably less than 0.018 inch, the extended sealable section has an effective length of at least 1 cm and more preferably at least 5 cm and an outer diameter of less than 0.050 inch and more preferably less than 0.012 inch, and the occlusive device (balloon) is deflated in less than two minutes and more preferably less than one minute. This embodiment is particularly adapted to provide distal embolization protection in debulking vascular interventional procedures, such as those involving a blocked saphenous vein coronary bypass graft. Alternatively, the guidewire assembly may be configured and dimensioned for use in peripheral vascular procedures or neurovascular procedures.

In a preferred embodiment, the inflation system of the gas inflation/evacuation system includes a plurality of individually actuatable syringes each containing a sufficient volume of biocompatible gas for a single inflation of the occlusive device so as to minimize the volume of biocompatible gas in the gas inflation/evacuation system in the event of a leak. The preferred embodiment is packaged in a sterile packaging that is assembled and packaged in a sealed chamber filled with a biocompatible gas such that any gas within the sterile packaging once packaged is only the biocompatible gas.

BRIEF DESCRIPTION OF THE DRAWINGS

FIGS. 4a and 4b are fragmentary cross-sectional views of different manners of joining the extended sealable section to the main body portion at the proximal portion of the guidewire assembly of FIG. 3a.

DETAILED DESCRIPTION OF THE PREFERRED EMBODIMENTS

Figure 1:
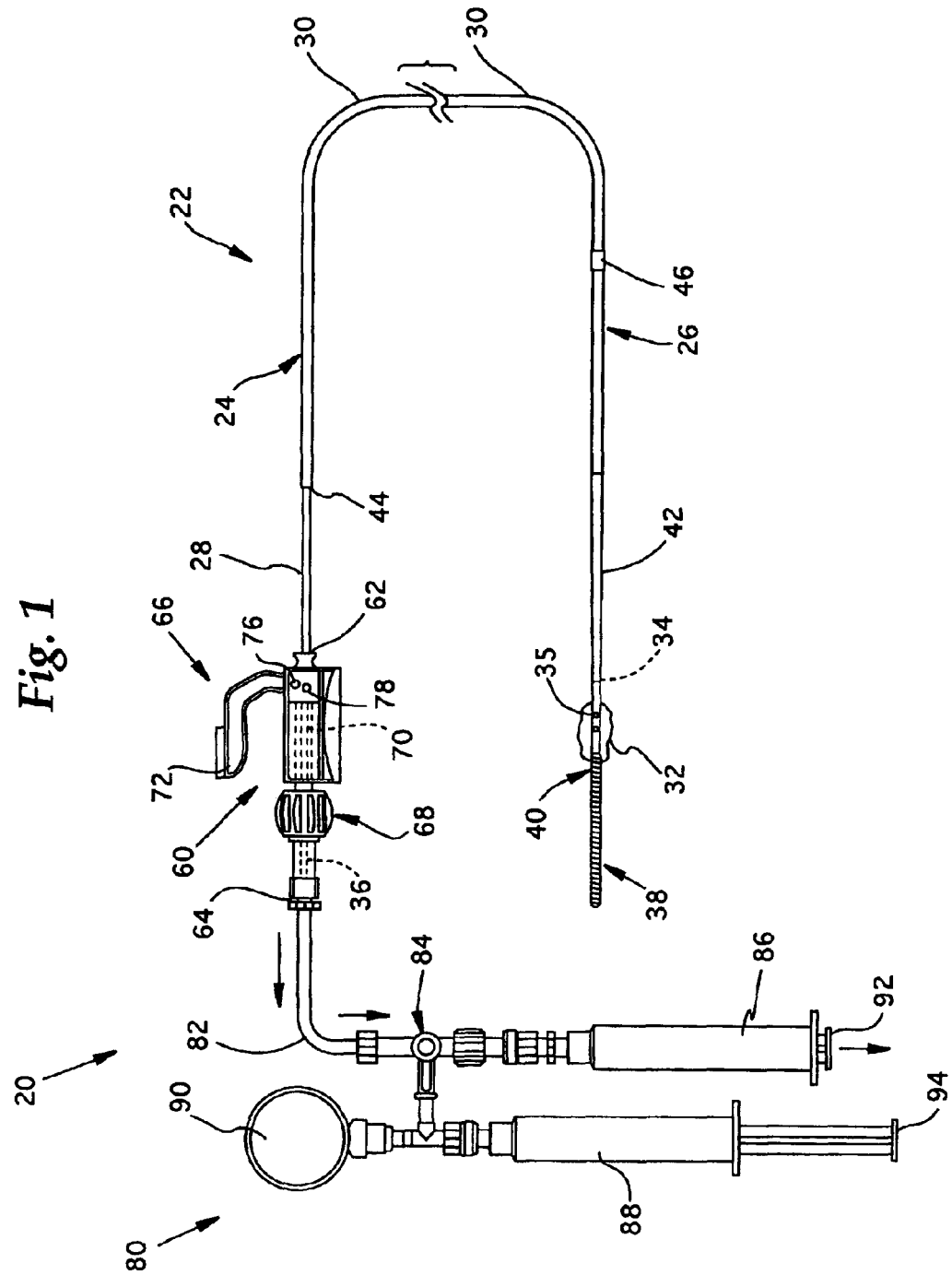
FIG. 1 is a schematic diagram of a guidewire occlusion system in accordance with the present invention and operating in an evacuation mode.
Figure 2:
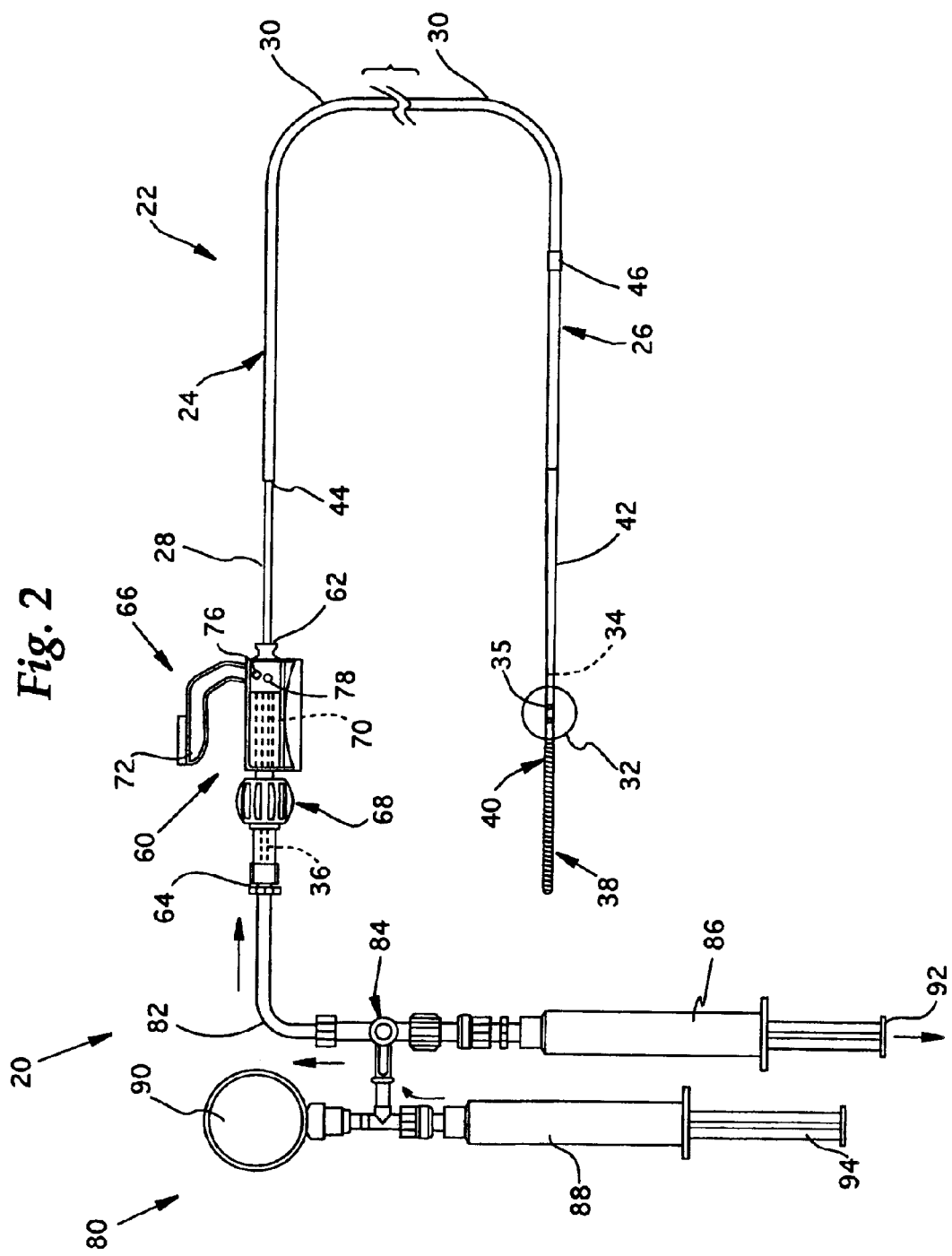
FIG. 2 is a schematic diagram of the guidewire occlusion system shown in FIG. 1 operating in an inflation mode.
Figure 3A:
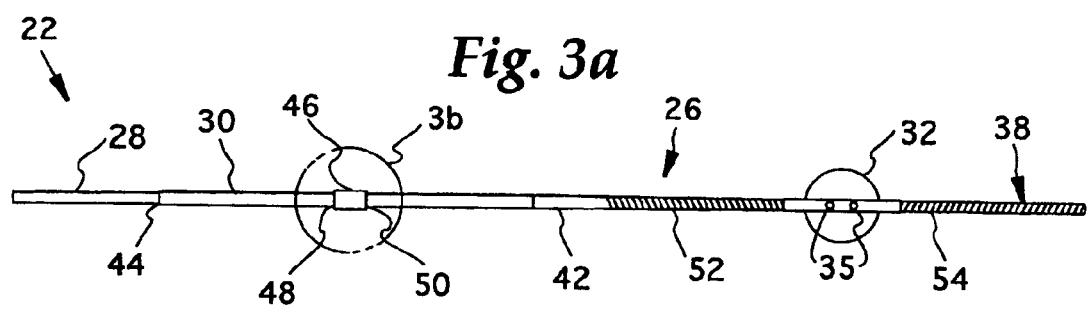
FIG. 3a is a side view of the guidewire assembly shown in FIG. 1.
Figure 3B:
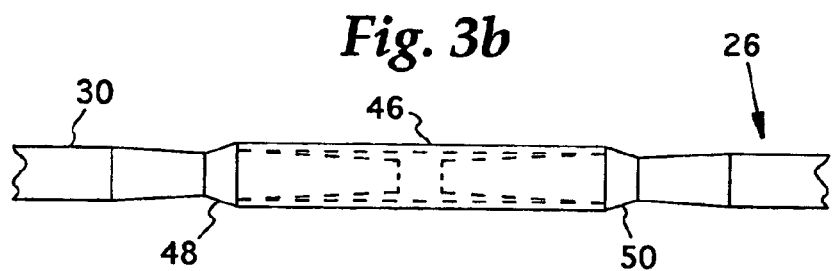
FIG. 3b is an enlarged view of the portion of FIG. 3a delineated by the circle 3b.

Referring now to FIGS. 1–2, the overall structure and operation of a guidewire occlusion system 20 in accordance with the present invention will be described. The guidewire occlusion system 20 includes a guidewire assembly 22, a sealing system 60, and a gas inflation/evacuation system 80.

Guidewire assembly 22 is a tubular member that includes a proximal portion 24 and a distal portion 26. As used in the present invention, the terms proximal and distal will be used with reference to an operator, such that a distal portion of the guidewire assembly 22, for example, is the portion first inserted into a blood vessel, and the proximal portion remains exterior to the patient and is therefore closer to the operator. An extended sealable section 28 is provided proximate the proximal portion 24 of guidewire assembly 22. Preferably, the extended sealable section 28 is an extended crimpable section comprised of a tubular segment having an outer diameter smaller than an outer diameter of a main body portion 30 of guidewire assembly 22. Although the diameter of the extended crimpable section could be any size consistent with effective use as a guidewire, it will be understood that the smaller diameter allows for less force to be used in sealing the extended crimpable section and provides a crimped seal that is not too large when crimped. An occlusive balloon 32 is located along the distal portion 26 of guidewire assembly 22. The occlusive balloon 32 is fluidly connected via a lumen 34 to the proximal end 36 of guidewire assembly 22, with channels or holes 35 allowing for fluid communication between lumen 34 and occlusive balloon 32. In a preferred embodiment, a flexible tip 38 is positioned at the distal end 40 of distal portion 26 of the guidewire assembly 22. Preferably, distal portion 26 of guidewire assembly 22 includes a tapered portion 42 to increase the flexibility and transition properties of the distal portion 26 of guidewire assembly 22.

Preferably, sealing system 60 is implemented as part of a handheld apparatus that also includes gas inflation/evacuation system 80. Alternatively, sealing system 60 may be a handheld unit completely separate from the gas inflation/evacuation system 80. Sealing system 60 includes a first aperture 62 into which the proximal end 36 of guidewire assembly 22 is insertable so as to operably position at least a portion of extended sealable section 28 in relation to sealing system 60. Sealing system 60 further includes a second aperture 64 that is fluidly connectible to gas inflation/evacuation system 80. The sealing system 60 includes means for selectively sealing the extended sealable section which in the preferred embodiment comprises a crimping mechanism 66 and a sealing mechanism 68. A passageway 70 is defined from first aperture 62 to second aperture 64 and extends through both crimping mechanism 66 and sealing mechanism 68. Preferably, at least a portion of the extended sealable section 28 is inserted into first aperture 62 a sufficient distance to engage crimping mechanism 66 and sealing mechanism 68.

Figure 12:
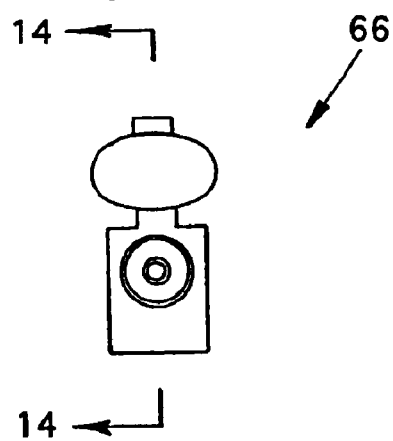
FIG. 12 is an end view of a crimping mechanism.
Figure 13:
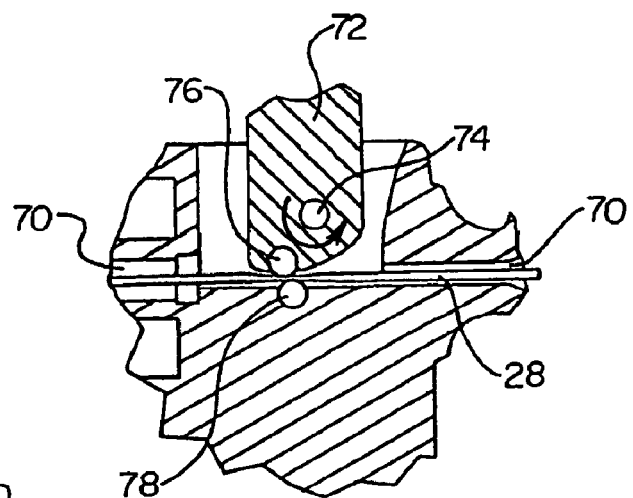
FIGS. 13 and 14 are two sectional views of the crimping mechanism of FIG. 12, FIG. 14 being a view taken along the line 14—14 of FIG. 12, and FIG. 13 being a magnification of the portion of FIG. 14 indicated by the dashed circle.
Figure 14:
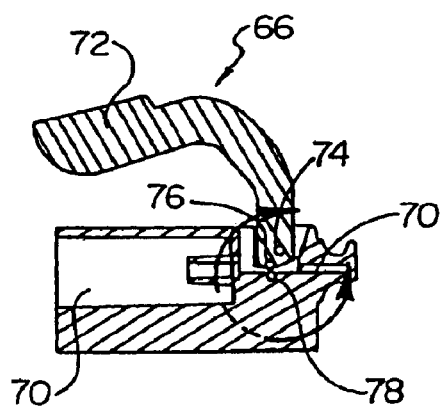

In a preferred embodiment of the crimping mechanism 66 as shown in FIGS. 12–14, the crimping mechanism 66 comprises a handle 72 that actuates a pivotable cam arrangement 74 that crimps and then severs the extended sealable section 28 between a pair of rollers 76, 78 by mechanically flattening and pinching the extended sealable section 28 to the point of breaking. Preferably, the sealing mechanism 68 has a rotatable hemostatic valve positioned proximal to the crimping mechanism 66 along passageway 70. Preferably, crimping mechanism 66 and sealing mechanism 68 are arranged coaxially with each other along a straight portion of passageway 70. In this embodiment, when the proximal end 36 of guidewire assembly 22 is inserted into first aperture 62 until the proximal end 36 engages the hemostatic valve of sealing mechanism 68, the extended sealable section 28 is properly positioned relative to the crimping mechanism 66.

It will be seen that the relative distance between the engaging portions of sealing mechanism 68 and crimping mechanism 66 in this embodiment effectively defines the relative distances between a plurality of locations along extended sealable section 28 at which an airtight seal can be created, as shown in FIGS. 1–2. To permit multiple inflations and deflations of the occlusive balloon 32 of the guidewire assembly 22, the length of the extended sealable section 28 should be greater than at least twice the distance between crimping mechanism 66 and sealing mechanism 68.

The gas inflation/evacuation system 80 is connected via conduit 82 to the second aperture 64 of the sealing system 60. The gas inflation/evacuation system 80 preferably includes a valve arrangement 84 that selectively couples one of an evacuation system which includes means for evacuating the guidewire assembly and an inflation system which includes means for introducing a gas into the guidewire assembly to the conduit 82. The evacuation system includes an evacuation syringe 86 which is used to evacuate the guidewire assembly 22, passageway 70, and conduit 82. The inflation system includes an inflation syringe 88 which contains a volume of a gas sufficient to inflate the occlusive balloon 32 a plurality of times. Optionally, a pressure gauge 90 can be associated with the inflation syringe 88.

Preferably, the gas is a biocompatible gas such as carbon dioxide. Other biocompatible gasses that may be utilized with the present invention include oxygen, nitrogen, and nitrous oxide. While non-biocompatible gasses could be used, biocompatible gasses that are soluble in blood are preferred so as not to cause gas embolization in the event of a leak in the gas inflation/evacuation system. Preferably, the biocompatible gas also has a good driving gradient in addition to being soluble, in that the biocompatible gas will effectively go into a solution, in this case blood, better than ambient air. Although not preferred, low viscosity biocompatible liquids or foams also may be used for inflation provided the surface tension of the fluid is sufficient to permit the rapid inflation and deflation contemplated by the present invention.

It will be understood that if the guidewire assembly 22, including the occlusive balloon 32, could be verified as being capable of repeated inflations and deflations without any leakage or bursting of the occlusive balloon, then the evacuation portion of the gas inflation/evacuation system 80 would not be necessary, as the evacuation portion of the gas inflation/evacuation system 80 is intended for safety purposes to ensure that air within the guidewire assembly 22 and sealing system 60 is not introduced into the blood stream in the event of a failure, leakage or bursting of any component.

Figure 4A:
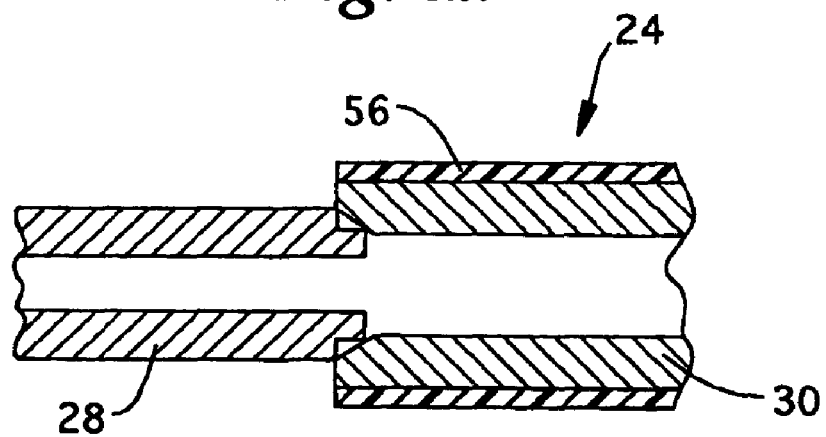
Figure 4B:
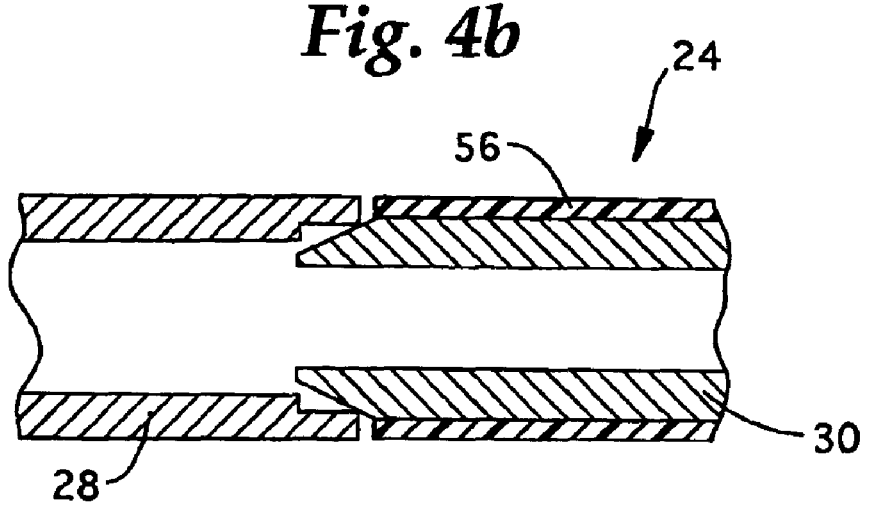

In a preferred embodiment shown in FIGS. 3a, 3b, 4a and 4b, guidewire assembly 22 is constructed as described in further detail in the previously identified co-pending application Ser. No. 10/012,891 entitled "Guidewire Assembly Having Occlusive Device And Repeatably Crimpable Proximal End." The main body portion 30 is formed of a primary stainless steel hypotube having an outer diameter of 0.013 inch and an inner diameter of 0.007 inch. To accomplish passive deflation in the desired time of less than one minute when the extended sealable section 28 is cut, it is preferable that the main body portion 30 have an inner diameter of at least 0.002 inch. The extended sealable section 28 of guidewire assembly 22 is comprised of a crimp tube also formed of stainless steel and having an outer diameter of 0.009 inch to 0.015 inch and an inner diameter of at least 0.002 inch and preferably about 0.005 inch. The extended sealable section 28 is preferably a separate piece secured to the proximal portion 24 by a laser weld 44 (see FIGS. 1, 2 and 3*a*) of sufficient strength. Alternatively, the extended sealable section 28 may be formed by centerless grinding or reducing the outer diameter of a portion of the proximal portion 24 of the main body portion 30 of guidewire assembly 22. Still other embodiments may enable the extended sealable section to be a modified, treated or otherwise fabricated portion of the proximal portion 24 of the main body portion 30 of guidewire assembly 22 that is suitable for the particular sealing technique to be used. As shown in FIG. 4*a*, in one embodiment the distal end of the extended sealable section 28 is preferably centerless ground and press fit within a chamfered proximal end of the main body portion 30. Alternatively, as shown in FIG. 4*b*, a chamfered crimp arrangement could be used. Still further, a separate joining/crimping tube or other tubular joining arrangements could be used. Preferably, a protective polymer coating 56 of polytetrafluoroethylene (PTFE) or a hydrophilic coating is applied by any of a number of known techniques such that the coating 56 surrounds the main body portion 30. The protective polymer coating 56 is preferably about 0.0004+/−0.0003 inch thick such that the effective outer diameter of the main body portion 30 of guidewire assembly 22 is 0.0132–0.0144 inch.

In this embodiment, the extended sealable section 28 can be made of any material that when deformed and severed retains that deformation so as to form an airtight seal. When crimped and severed, it is preferable that the extended sealable section 28 not present a sharp, rigid point that is capable of piercing a gloved hand. It has been found that as long as the preferred embodiment is not gripped within less than one inch of the proximal end of the extended sealable section 28, the severed proximal end of the extended sealable section 28 does not penetrate a standard surgical glove. In addition, the extended sealable section 28 must have sufficient strength in terms of high tensile and kink resistance to permit catheter devices to repeatedly pass over the extended sealable section 28.

In this embodiment, the main body portion 30 is preferably secured to the distal portion 26 using a Ni—Ti or stainless steel sleeve 46 laser welded to the main body portion 30 at laser weld 48 and crimped to the distal portion 26 at crimp 50. The distal portion 26 is preferably formed of a Ni—Ti alloy having an inner diameter of 0.0045 inch and an outer diameter that ranges from 0.014 inch to 0.0075 inch to form tapered portion 42, preferably formed by a centerless grinding process. Preferably, the distal portion includes a pair of coil sections, proximal tip coil 52 and distal tip coil 54, that are longitudinally spaced apart and adjacent to the holes 35 and that assist in providing a better surface for bonding the occlusive balloon 32 to the distal portion 26. This arrangement also tends to increase the visibility of the location of the occlusive balloon 32 under fluoroscopy, as the occlusive balloon 32 filled with a biocompatible gas will be radiotranslucent when compared to the two coils 52 and 54. Alternatively, a platinum markerband could be located around the distal portion 26 just proximal to the occlusive balloon 32 to serve as a radiopaque/MRI marker. The flexible tip 38 is a coiled tip attached to distal portion 26 distal to occlusive balloon 32, preferably by a crimp. Alternatively, a sleeve could be welded to the flexible tip 38, and the tapered portion 42 could then be inserted into this sleeve and crimped.

Alternatively, any number of other alloys or polymer materials and attachment techniques could be used in the construction of the guidewire assembly 22, provided the materials offer the flexibility and torque characteristics required for a guidewire and the attachment techniques are sufficiently strong enough and capable of making an airtight seal. These materials include, but are not limited to, Ni—Ti, 17-7 stainless steel, 304 stainless steel, cobalt superalloys, or other polymer, braided or alloy materials. The attachment techniques for constructing guidewire assembly 22 include, but are not limited to, welding, mechanical fits, adhesives, sleeve arrangements, or any combination thereof.

The occlusive balloon 32 may be made of any number of polymer or rubber materials. Preferably, the occlusive balloon is preinflated to prestretch it so that expansion is more linear with pressure. Preferably, the pressure supplied by gas inflation/evacuation system 80 is designed to stay well within the elastic limit of the occlusive balloon 32. A two-layer occlusive balloon arrangement, adding gas and/or liquid between balloon layers, may be used in an alternate embodiment to increase visibility of the distal end 40 of the distal portion 26 of the guidewire assembly 22 under fluoroscopy.

In practice, medical personnel gain entry to the vessel lumen prior to use of the guidewire occlusion system 20. The extended sealable section 28 of the proximal portion 24 of guidewire assembly 22 is inserted into first aperture 62 and connected via sealing mechanism 68. The distal portion 26 of guidewire assembly 22 is inserted into the vessel lumen, and occlusive balloon 32 is inserted to a point distal to the vessel occlusion. Valve arrangement 84 is set for evacuation. Evacuation syringe plunger 92 of evacuation syringe 86 is slidably withdrawn removing any air from guidewire assembly 22. Valve arrangement 84 is then set for inflation. Inflation syringe plunger 94 of inflation syringe 88 is slidably advanced inserting a volume of an inert gas into guidewire assembly 22. The inert gas inflates occlusive balloon 32 as shown in FIG. 2. During inflation, the medical personnel monitor pressure gauge 90 to ensure that the inflation pressure does not exceed the burst rating of the occlusive balloon 32 and to gauge the relative size of the occlusive balloon 32 as it is inflated. Following inflation of occlusive balloon 32, crimping mechanism 66 is employed to crimp the extended sealable section 28 of guidewire assembly 22, thereby sealing the guidewire assembly 22 to maintain the occlusive balloon 32 in an inflated state. Sealing mechanism 68 is released and the extended sealable section 28 is removed from first aperture 62 such that the proximal portion 24 of the guidewire assembly 22 is free of mechanical or other obstructions and can function as a conventional guidewire. When the medical personnel decide to deflate the occlusive balloon 32, the extended sealable section 28 is cut using a medical scissors or the like distal to the existing crimp in the extended sealable section 28. When the medical personnel deem reinflation of the occlusive balloon 32 to be necessary, the extended sealable section 28 of the proximal portion 24 is reinserted into first aperture 62. Sealing mechanism 68 is then reactivated and the evacuation/inflation process can be repeated. It will be understood that a crimping handle 72 may also be provided with a separate severing arrangement to cut the extended sealable section 28. Alternatively, extended sealable section 28 may be scored or otherwise weakened in selected locations to assist in crimping or severing, including severing by repeated bending back and forth at one of the scored locations. In another embodiment, the extended sealable section 28 could be broken off rather than sheared by using a brittle metal for the extended sealable section that aids in the severing of the extended sealable section 28.

Figure 5:
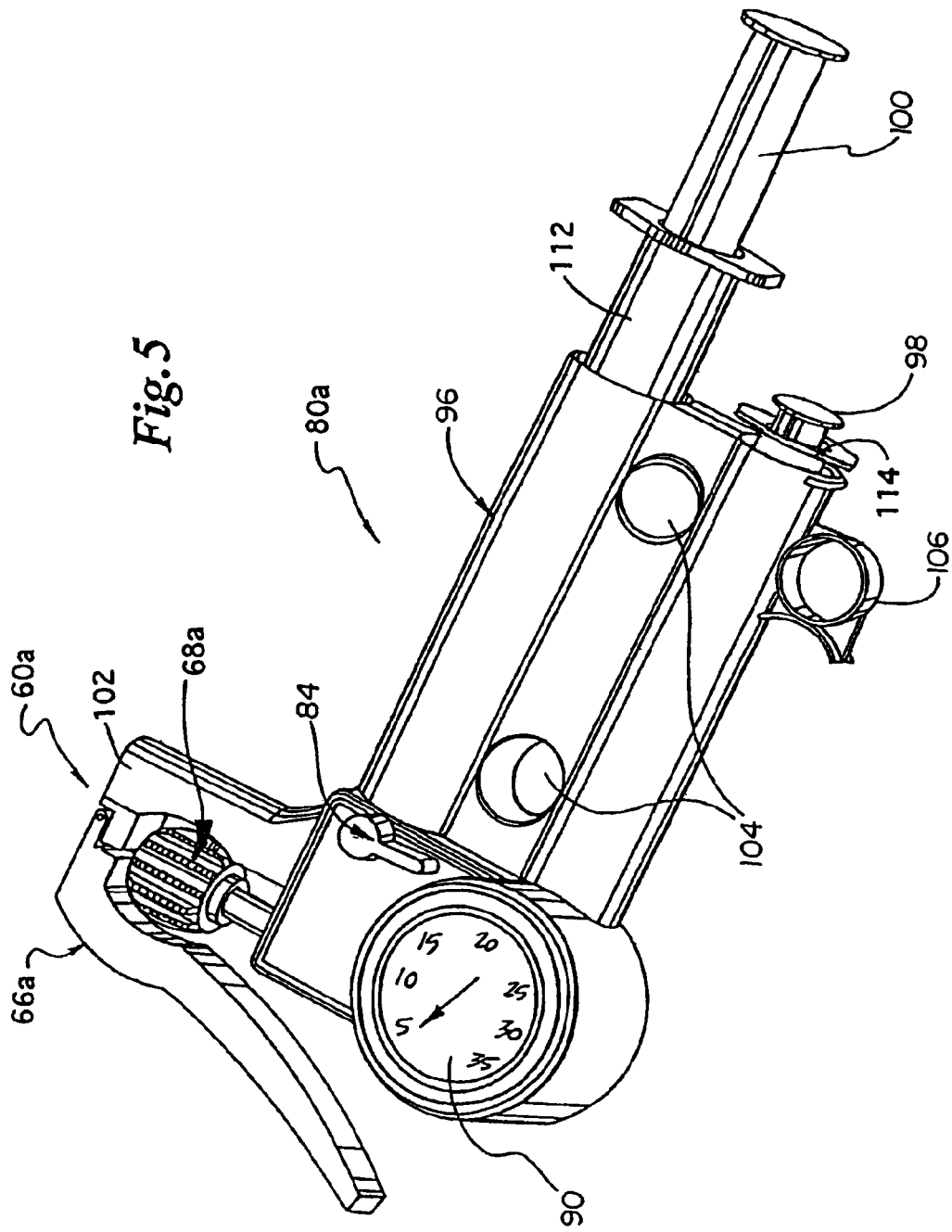
FIGS. 5–7 are perspective views of three alternate embodiments of gas inflation/evacuation systems and the sealing systems used therewith.

FIG. 5 shows an alternative unitized gas inflation/evacuation system 80a and also an alternative sealing system 60a. Assembly body 96 contains individual inflation syringe 114 with inflation syringe plunger 98 and individual evacuation syringe 112 with evacuation syringe plunger 100. Assembly body 96 contains pressure gauge 90. Attached to assembly body 96 is support structure 102 which supports a sealing system 60a that includes crimping mechanism 66a and sealing mechanism 68a. Valve arrangement 84 is mounted on the surface of assembly body 96. Assembly body 96 contains two fingergrip bores 104. Attached to assembly body 96 is fingergrip 106. In the preferred embodiment, the assembly body 96 is constructed of a suitable inert plastic polymer, although any polymer material used in construction of medical devices could be used. In another embodiment, the assembly body 96 can be constructed of suitable metal alloys or even of tempered glass or any combination thereof.

Figure 6:
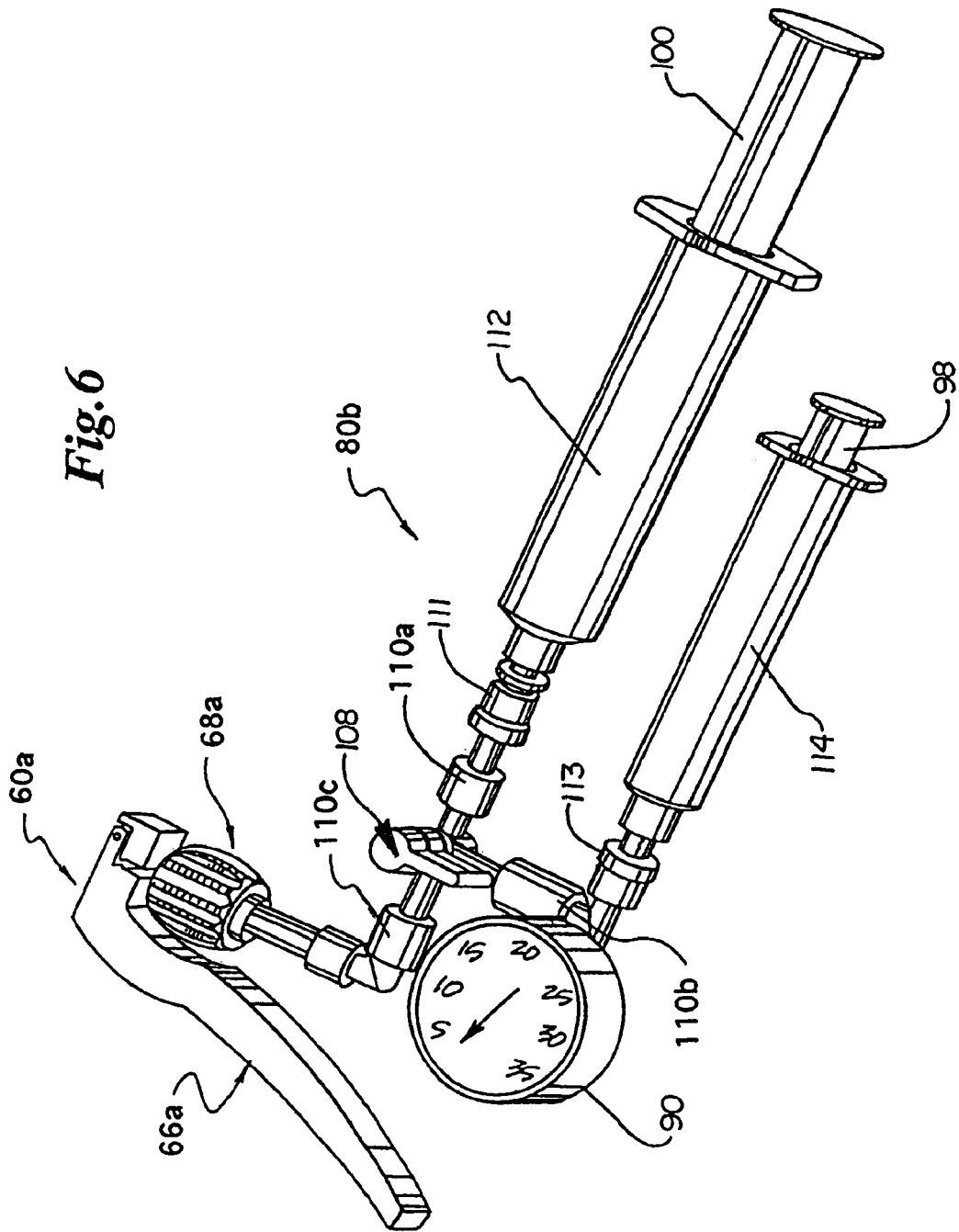

FIG. 6 shows an alternative gas inflation/evacuation system 80b in use with sealing system 60a. Valve arrangement 108 has three interconnect fittings 110a, 110b and 110c. Attached to interconnect fitting 110a is evacuation syringe 112. Evacuation syringe 112 includes evacuation syringe plunger 100. Attached to interconnect fitting 110b is pressure gauge 90. Pressure gauge 90 is fluidly interconnected to inflation syringe 114. Inflation syringe 114 includes inflation syringe plunger 98. Attached to the interconnect fitting 110c is sealing system 60a comprised of crimping mechanism 66a and sealing mechanism 68a. Preferably, one-way check valves 111 and 113 are respectively connected between interconnect fitting 110a and evacuation syringe 112 between interconnect fitting 110b and inflation syringe 114 as a safety measure to ensure only one-way flow of the gas within the gas inflation/evacuation system 80b. One-way check valve 113 ensures that only the carbon dioxide gas is delivered out of the gas inflation/evacuation system and prevents any reinfusion of air that has been evacuated from the gas inflation/evacuation system.

Figure 7:
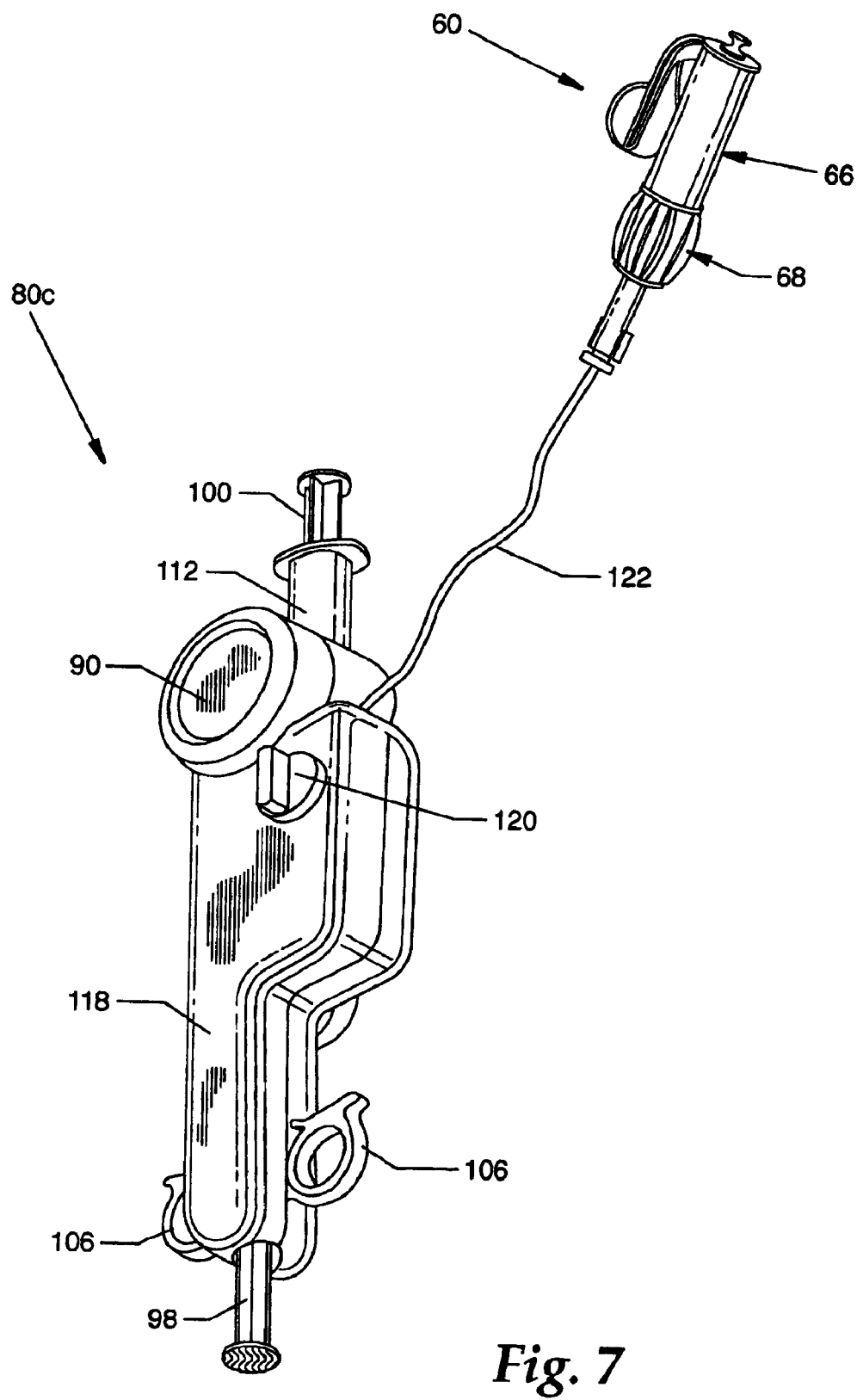
Figure 8:
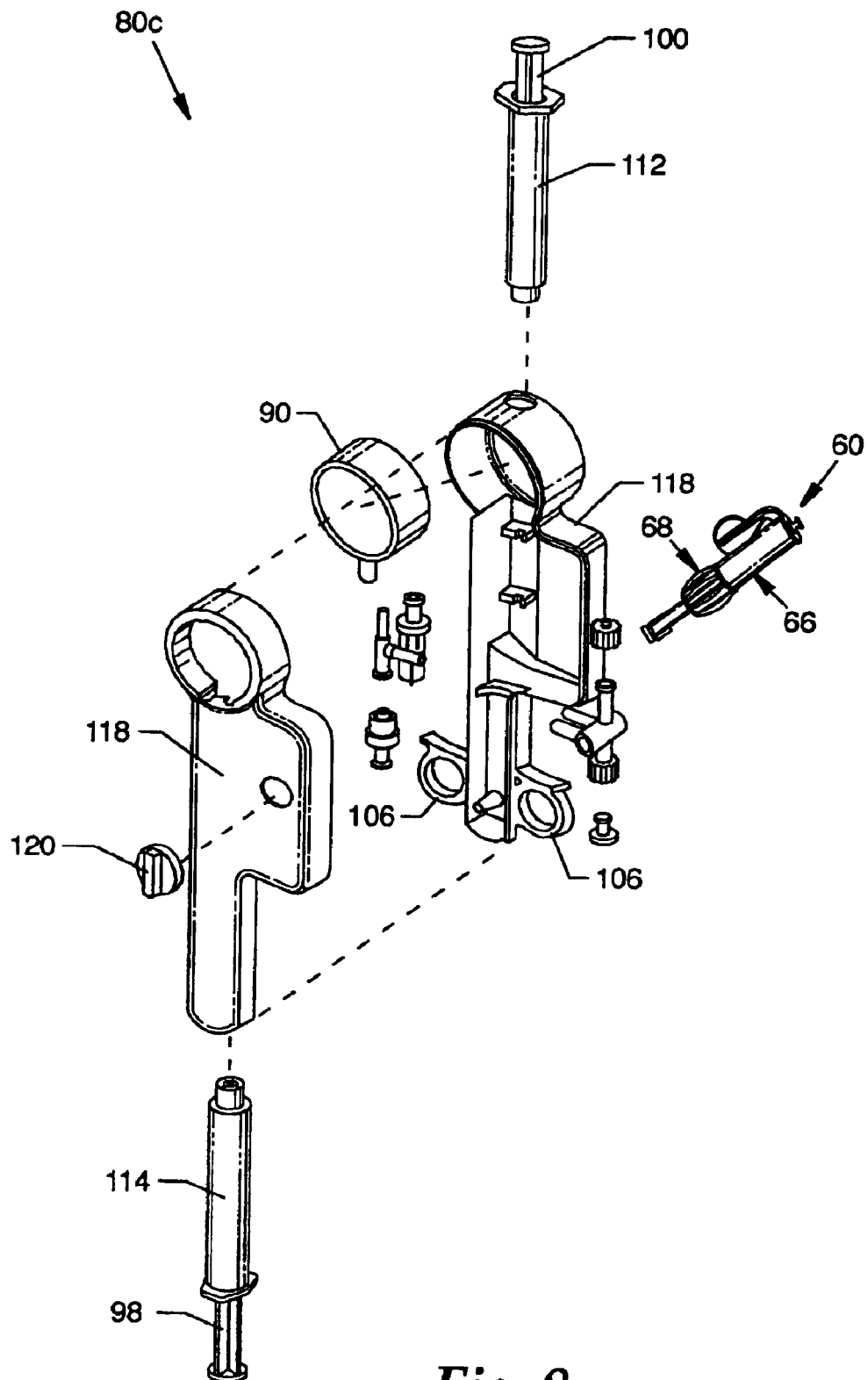
FIG. 8 is an exploded view of the gas inflation/evacuation system of the alternate embodiment shown in FIG. 7 and the associated sealing system.

FIGS. 7 and 8 show an alternative gas inflation/evacuation system 80c with sealing system 60. Assembly body 118 contains inflation syringe 114 and evacuation syringe 112. Inflation syringe 114 includes inflation syringe plunger 98. Evacuation syringe 112 includes evacuation syringe plunger 100. Knob 120 connected to valve arrangement 108 is mounted on the exterior of assembly body 118. Pressure gauge 90 is contained within assembly body 118. Assembly body 118 contains fingergrips 106. Conduit 122 is attached to assembly body 118. At the distal end of conduit 122 is sealing system 60 which is comprised of crimping mechanism 66 and sealing mechanism 68.

Figure 9:
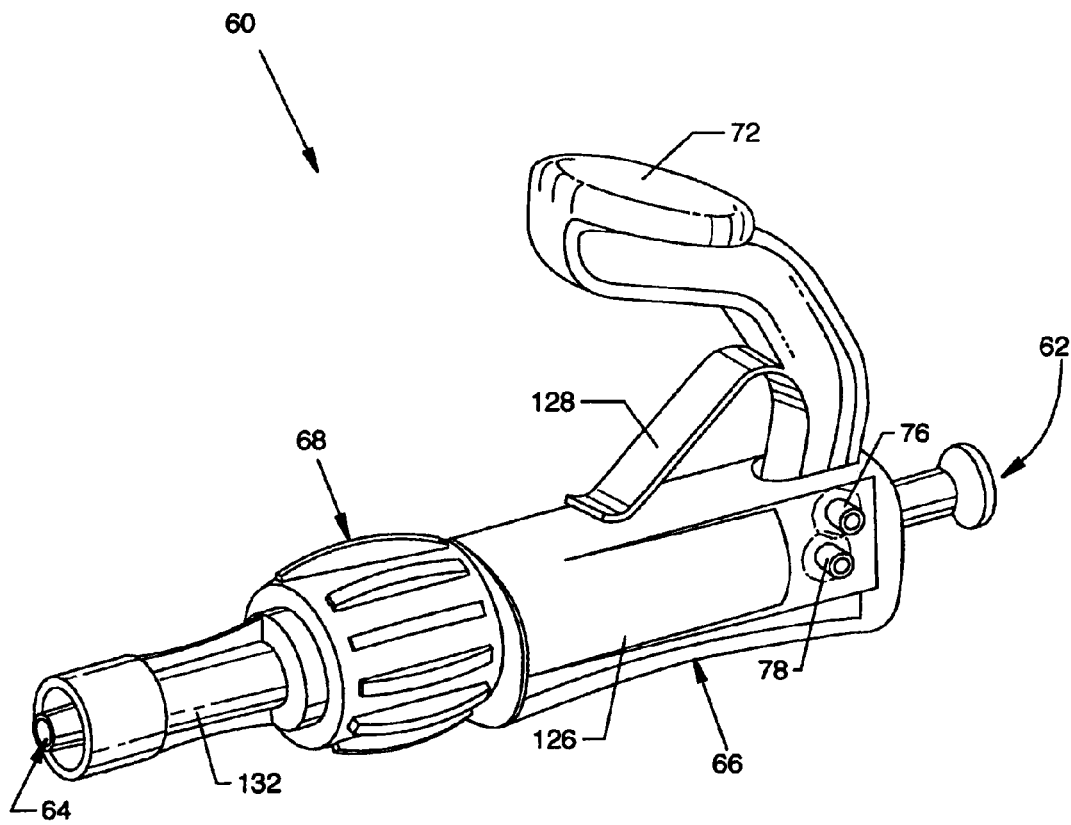
FIG. 9 is a perspective view of the sealing system illustrated with the alternate embodiment shown in FIG. 7.

FIG. 9 shows an embodiment of the sealing system. Specifically, FIG. 9 shows sealing system 60 which is comprised of sealing mechanism 68 and crimping mechanism 66. Crimping mechanism 66 is comprised of crimp body 126, handle 72, handle return 128, and first aperture 62. Sealing mechanism 68 is comprised of sealing body 132 and second aperture 64. Sealing system 60 has a passageway 70 (see FIGS. 1 and 2) fluidly interconnecting first aperture 62 and second aperture 64.

Figure 10:
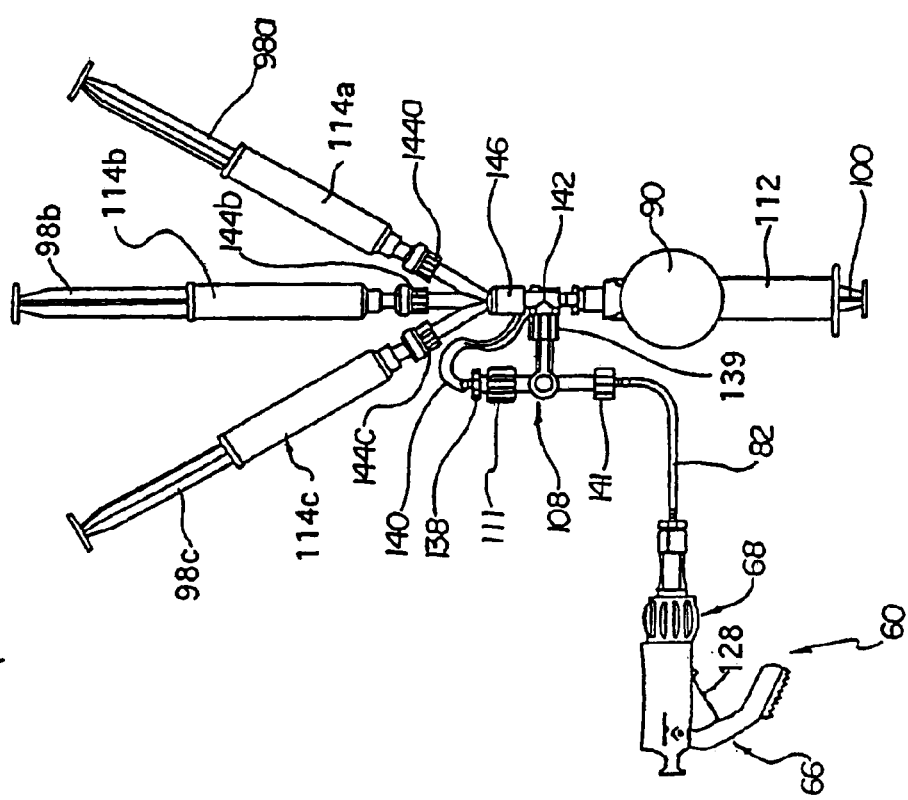
FIG. 10 is a top view of a preferred embodiment of a gas inflation/evacuation system and sealing system used in the present invention.

FIG. 10 shows an alternative gas inflation/evacuation system 80d coupled to sealing system 60. Valve arrangement 108 has a coupling 141 connected to conduit 82 and a port 138 that is attached via one-way check valve 111 and hose 140 to evacuation syringe 112. Attached to an interconnect fitting 139 of the valve arrangement 108 is inflation manifold 142. Inflation manifold 142 is connected to connector 146 and pressure gauge 90. Inflation manifold 142 has three check valves 144a, 144b and 144c. Check valves 144a, 144b and 144c are connected to respective inflation syringes 114a, 114b and 114c which have respective inflation syringe plungers 98a, 98b, and 98c. In this embodiment, evacuation syringe 112 is mounted behind pressure gauge 90. As with the other embodiments, the distal end of conduit 82 is connected to sealing system 60. Sealing system 60 is comprised of sealing mechanism 68 and crimping mechanism 66.

Figure 11:
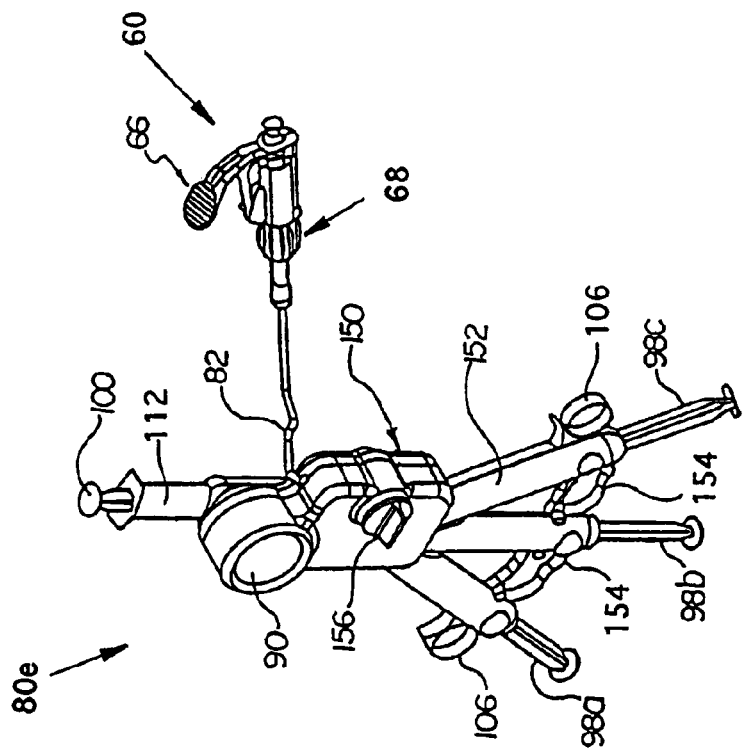
FIG. 11 is a perspective view of another alternate embodiment of a gas inflation/evacuation system and sealing system.

FIG. 11 shows an alternative gas inflation/evacuation system 80e that is similar to the gas inflation/evacuation system 80d shown in FIG. 10 except that the components are arranged in a common housing 150. Common housing 150 has internal sealed channels that fluidly interconnect via valve arrangement 108 to evacuation syringe 112 and to inflation syringes 114a, 114b and 114c and pressure gauge 90. Common housing 150 has structure 152 that defines chambers for the three inflation syringes 114a, 114b and 114c. Common housing 150 also includes structure defining external fingergrips 106 and internal fingergrips 154 between adjacent portions of structure 152. Common housing 150 also contains structure for integrating evacuation syringe 112 and pressure gauge 90 as part of the common housing 150. An external knob 156 connects to the valve arrangement 108.

The embodiments shown in FIGS. 10 and 11 allow for effective pressurization of occlusive balloon 32 at less than 2 atmospheres while reducing the total volume of gas that might be introduced into a patient in the event of a leak in the guidewire occlusion system 20. Depending upon the desired inflation pressure and the total number of inflation cycles, the total amount of pressurized gas in a single inflation syringe such as 88 in FIGS. 1 and 2 or 114 in FIGS. 5–8 can be significant. If a leak were to occur, the entire contents of a single inflation syringe would be susceptible to that leak. By using a separate inflation syringe 114a, 114b, 114c for each inflation in the embodiments shown in FIGS. 10 and 11, these alternate embodiments provide a simple way of decreasing the total amount of pressurized gas that might be introduced into a patient in the event of a leakage in the guidewire occlusion system 20.

A similar result could be achieved by manually attaching separate inflation syringes 114a, 114b, 114c and an evacuation syringe 112 directly to the sealing system 60 by way of a Luer lock or the like. While such an embodiment would not be as quick or convenient as the preferred embodiment, such alternative would eliminate the volume of gas required for the conduit 82 and within common housing 150, as well as the need for a valve arrangement 108.

Figure 15:
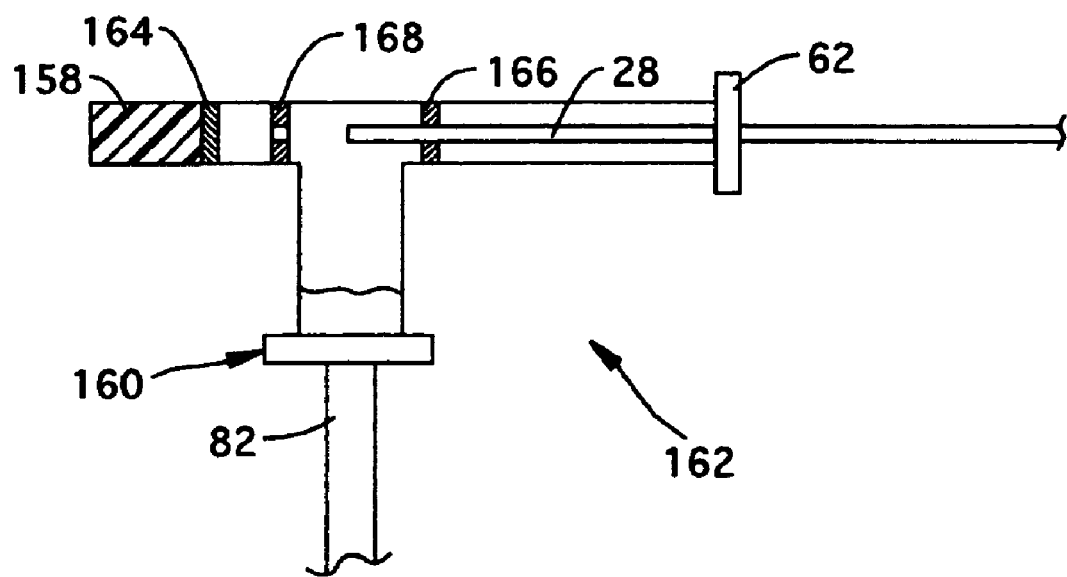
FIG. 15 is a cross-sectional view of an alternate embodiment of a sealing system showing one embodiment of a plugging mechanism.

In alternate embodiments, the sealing system could include means for selectively sealing involving techniques other than crimping to accomplish multiple airtight seals along the course of the extended sealable section 28. One alternate embodiment, as portrayed in FIG. 15, would involve the insertion of some form of sealant material 158 into the proximal end of the extended sealable section 28, such as wax, plastic, polymer or metal inserts or plugs. Conduit 82 is attached to plugging mechanism 162 through the conduit aperture 160. In this embodiment, sealant material 158 is confined by sealant confinement layer 164 residing within plugging mechanism 162. Preferably for this embodiment, sealant material 158 is a wax or gel that is flowable at higher temperatures and might be melted during sterilization of the sealing system. Sealant confinement layer 164 is a foil layer or thin layer of non-meltable material capable of confining a flowable material during any sterilization process or exposure to higher temperature. The proximal end of extended sealable section 28 is inserted through first aperture 62 until it is past operational O-ring 166 or some other form of sealable/deformable material such as a silicone puncture seal or similar membrane seal. When it is desired to seal the extended sealable section 28, the extended sealable section 28 is further inserted past a sealant O-ring 168, then through sealant confinement layer 164, and finally into sealant material 158. Sealant material 158 is deposited in the proximal end of extended sealable section 28, thus preventing the guidewire assembly 22 from being evacuated. Extended sealable section 28 can then be slidably withdrawn through the sealant O-ring 168, through the operational O-ring 166, and through the first aperture 62, thereby effectively disengaging the guidewire assembly 22 from the plugging mechanism 162. The O-rings 166 and 168 serve as wiping structures to remove excess sealant material from the outside of the extended sealable section 28. Other alternate embodiments involve heating the extended sealable section 28 when it is formed of metal or polymer material so as to create a constriction, or applying electrical or magnetic energy to arc or weld material within the extended sealable section 28 to create a constriction. In one embodiment, the equivalent of a spot welder could be used in place of the crimping mechanism 66 to accomplish the same purpose of sealing, and then severing the extended sealable section 28. Alternative embodiments could use other sealing techniques to seal the guidewire assembly 22. These methods could include, but are not limited to, ones utilizing a heat source to melt the extended sealable section, ones using a heat source to apply a glue or gel, methods involving insertion of a plug material, methods using magnetics to manipulate a sealing material, or methods utilizing small occlusive devices.

Depending on the sealing method specified in an embodiment, different deflation techniques can be utilized. For the preferred embodiment, the extended sealable section 28 is of sufficient length to allow deflation through the shearing, breaking or opening of the extended sealable section 28 distal to the sealant material 158 located in the proximal end of the extended sealable section 28. By having sufficient length of the extended sealable section 28, the guidewire assembly 22 can be coupled to the gas inflation/evacuation system 80 (or 80a–80e) multiple times, allowing the occlusive balloon 32 to be inflated and deflated multiple times. Other embodiments will use methods of deflation including melting the sealant material 158, removing a plug of sealant material 158, and various other methods not requiring the extended sealable section 28 to be sheared.

Figure 16:
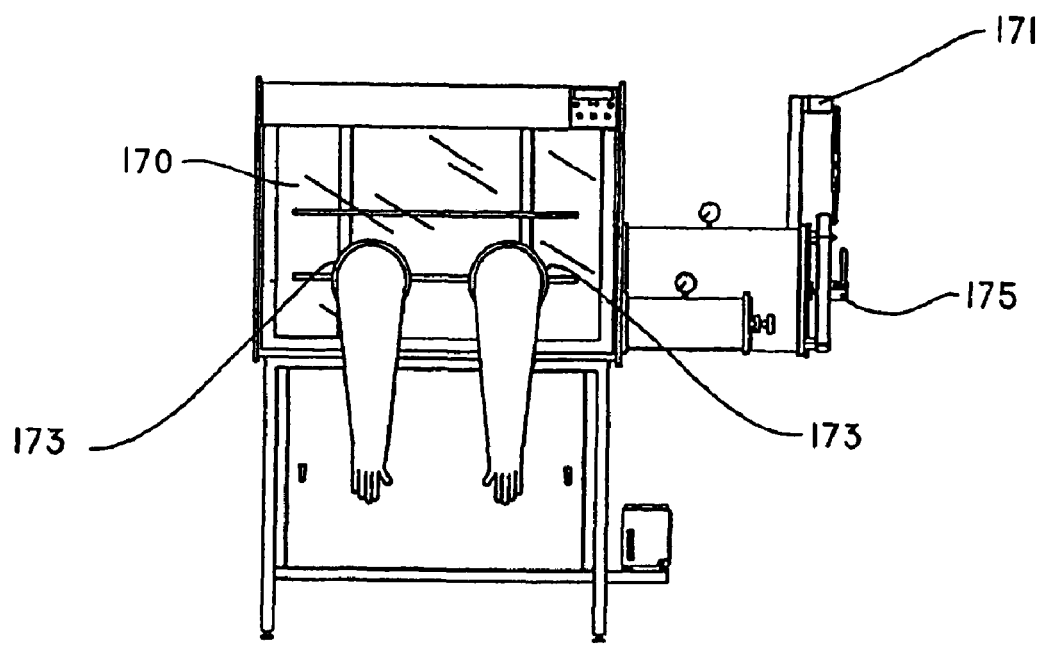
FIGS. 16 and 17 are schematic views relating to assembling and packaging the guidewire occlusion system, FIG. 16 showing equipment including a sealed chamber for use in assembling and packaging, and FIG. 17 showing a side view of a biocompatible packaging.
Figure 17:
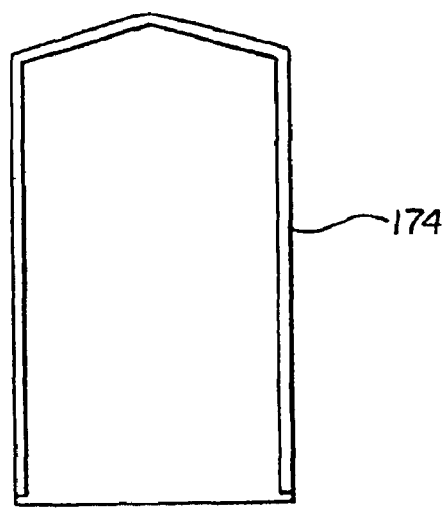

In one embodiment, the guidewire occlusion system 20 is preferably pre-assembled and packaged in an environment consisting of an appropriate biocompatible gas. FIGS. 16 and 17 show equipment with which the guidewire occlusion system 20 is assembled and packaged. The guidewire occlusion system 20 is assembled and packaged in a sealed chamber 170. Sealed chamber 170 is equipped with a venting duct 171, sealed handling ports 173, and an atmosphere control system 175. Sealed chamber 170 has an atmosphere composed of biocompatible gas. The guidewire assembly 22, sealing system 60 (or 60a), and gas inflation/evacuation system 80 (or 80a–80e) are assembled to form the guidewire occlusion system 20 and are placed into biocompatible packaging 174. Biocompatible packaging 174 is hermetically sealed so that the internal volume of both biocompatible packaging 174 and guidewire occlusion system 20 is composed solely of biocompatible gas.

The preferred embodiments of the various gas inflation/evacuation systems are described in further detail in the previously identified co-pending application Ser. No. 10/007,788 entitled "Gas Inflation/Evacuation System and Sealing System for Guidewire Assembly Having Occlusive Device".

In practice, medical personnel gain access to the vessel lumen through which the guidewire assembly 22 will travel. The guidewire occlusion system 20 is removed from biocompatible packaging 174. Flexible tip 38 is inserted in the vessel lumen and is manipulated to a point beyond the vessel occlusion. Valve arrangement 84 (or 108) is adjusted to the evacuation position and evacuation syringe plunger 92 (or 100) is slidably withdrawn to remove any gas present in the guidewire assembly 22. Valve arrangement 84 (or 108) is then adjusted to the inflation position and inflation syringe plunger 94 (or 98, 98a, 98b, 98c) is slidably inserted causing occlusive balloon 32 to inflate.

Following inflation of occlusive balloon 32, handle 72 of the crimping mechanism 66 (or the handle of 66a) is depressed causing roller 76 and roller 78 to crimp and preferably sever the extended sealable section 28 of guidewire assembly 22. Severing of the extended sealable section 28 serves as an immediate verification of the creation of an effective seal. Sealing mechanism 68 (or 68a) can be released and guidewire assembly 22 can be completely removed from the sealing system 60 (or 60a) allowing the occlusive balloon 32 to remain inflated while occlusive substance treatment occurs. Following treatment, the extended sealable section 28 can be sheared or broken off, resulting in the deflation of the occlusive balloon 32. If occlusive treatment is complete, guidewire assembly 22 can be removed from the vessel lumen. If additional treatment is required, extended sealable section 28 can be reattached to sealing system 60 (or 60a) through first aperture 62. Sealing mechanism 68 (or 68a) can be retightened and the evacuation/inflation process can be repeated.

In a preferred embodiment of the present invention, the guidewire assembly 22 is utilized as the guidewire for an atherectomy or thrombectomy procedure of the type described in U.S. Pat. Nos. 5,370,609 or 5,496,267, the disclosures of both of which are hereby incorporated by reference. In each of these procedures, the guidewire assembly 22 is introduced into the patient, the occlusive balloon 32 is inflated, and then the atherectomy or thrombectomy catheter arrangement is slid over the proximal end 36 of the guidewire assembly 22 and advanced until it is proximate and proximal to the location of the occlusive balloon. The procedure is performed for a time period consistent with the desired maximum length for blockage of the particular vessel, typically within 5 minutes, at which time the extended sealable section 28 of the guidewire assembly 22 may be severed to deflate the occlusive balloon 32, thereby reestablishing blood flow within the vessel. Depending upon the nature of the procedure, the catheter arrangement may be removed from the vessel or left in place. Preferably, an evacuation of any plaque material or other debris dislodged by the therapy is accomplished before deflation of the occlusive balloon 32. The occlusive balloon 32 is reinflated prior to reinitiation of the procedure.

It will be understood that because gas is used as the inflation medium instead of liquid, the wall thickness and therefore the stiffness of tubular members of the guidewire assembly 22 can be increased to effectively match the stiffness and flexibility of an ideal solid guidewire. Stiffness increase is dramatic as a result because stiffness of the tube is governed by the equation $(R(o)^{}4 - R(i)^{}4)$, such that an increase in wall thickness effectively quadruples the increase in stiffness of the guidewire assembly.

Rapid inflation and deflation of an occlusive balloon is the key to a successful occlusion device. The viscosity of the inflation fluid and resistance through the evacuation/inflation lumens dictate the effective speed of inflation and deflation. By lowering the viscosity of the inflation fluid, the present invention is able to increase the amount of resistance through the evacuation/inflation lumen that can be overcome. This results in being able to use a smaller inner diameter tube for the evacuation/inflation lumen which allows for a significant increase in the structural robustness of the guidewire assembly while maintaining the desired inflation and deflation properties. The increase in allowable resistance also allows for the use of longer guidewire assemblies, specifically guidewire assemblies that are a more typical exchange length. With typical high viscosity inflation fluids used to inflate liquid occlusive balloons, for example, it is not practical to develop an exchange length guidewire assembly because of the long deflation times associated with evacuation of the high viscosity inflation fluid through a much longer lumen.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

GUIDEWIRE OCCLUSION SYSTEM UTILIZING REPEATABLY INFLATABLE GAS-FILLED OCCLUSIVE DEVICE

PARTS LIST 20 guidewire occlusion system
22 guidewire assembly
24 proximal portion
26 distal portion
28 extended sealable section
30 main body portion
32 occlusive balloon
34 lumen
35 channel or hole
36 proximal end
38 flexible tip
40 distal end
42 tapered portion
44 laser weld
46 Ni—Ti or stainless steel sleeve
48 laser weld
50 crimp
52 proximal tip coil
54 distal tip coil
56 protective polymer coating
60 sealing system
60a sealing system
62 first aperture
64 second aperture
66 crimping mechanism
66a crimping mechanism
68 sealing mechanism
68a sealing mechanism
70 passageway
72 handle
74 pivotable cam arrangement
76 roller
78 roller
80 gas inflation/evacuation system
80a–e gas inflation/evacuation systems
82 conduit
84 valve arrangement
86 evacuation syringe
88 inflation syringe
90 pressure gauge
92 evacuation syringe plunger
94 inflation syringe plunger
96 assembly body
98 inflation syringe plunger
98a–c inflation syringe plungers
100 evacuation syringe plunger
102 support structure
104 fingergrip bore
106 fingergrip
108 valve arrangement
110a–c interconnect fittings
112 evacuation syringe
113 one-way check valve
114 inflation syringe
114a–c inflation syringes
118 assembly body
120 knob
122 conduit
126 crimp body
128 handle return
132 sealing body
138 port
139 interconnect fitting
140 hose
141 coupling
144a–c check valves
146 connector
150 common housing
152 structure
156 knob
158 sealant material
160 conduit aperture
162 plugging mechanism
164 sealant containment layer
166 O-ring
168 O-ring
170 sealed chamber
171 venting duct
173 sealed handling port
174 biocompatible packaging
175 atmosphere control system

What is claimed is:

1. A guidewire occlusion system for use in vascular procedures comprising:
   (a) a tubular guidewire assembly having an occlusive balloon proximate a distal end and an extended sealable section proximate a proximal end;
   (b) a gas inflation/evacuation system removably connectible to the proximal end of the tubular guidewire assembly, including:
      (1) means for evacuating the tubular guidewire assembly; and,
      (2) means for introducing a gas into the tubular guidewire assembly to inflate the occlusive balloon a plurality of times; and,
   (c) a sealing system removably connectible to the proximal end of the tubular guidewire assembly, including:
      (1) means for selectively sealing the tubular guidewire assembly by forming successive permanent airtight seals at separate locations along the extended sealable section to retain the gas in the occlusive balloon a plurality of times, wherein the diameter of the extended sealable section when sealed is no greater than the diameter of any other portion of the tubular guidewire assembly so that the tubular guidewire assembly may be used as a guidewire to introduce a catheter over the guidewire while gas is retained in the occlusive balloon.

2. The system of claim 1 wherein the tubular guidewire assembly has an effective length of at least 40 cm and an outer diameter of less than 0.060 inch, wherein the extended sealable section has an effective length of at least 1 cm and an outer diameter of less than 0.050 inch, and wherein the occlusive balloon can be deflated in less than two minutes.

3. The system of claim 1 wherein the tubular guidewire assembly has an effective length of at least 100 cm and an outer diameter of less than 0.018 inch, wherein the extended sealable section has an effective length of at least 5 cm and an outer diameter of less than 0.012 inch, and wherein the occlusive balloon can be deflated in less than one minute.

4. The system of claim 1 wherein the extended sealable section comprises an extended crimpable section and the means for selectively sealing comprises a crimping mechanism which permanently deforms and crimps the extended crimpable section.

5. The system of claim 4 wherein the extended crimpable section is dimensioned and the crimping mechanism is arranged such that an effective outer diameter of the extended crimpable section at the location of a seal is no greater than the outer diameter of a main body portion of the tubular guidewire assembly when the extended crimpable section is crimped at the location of the seal.

6. The system of claim 1 wherein the occlusive balloon is capable of repeated inflation and deflation during a vascular procedure in between which the proximal end of the tubular guidewire assembly is free of mechanical connections and obstructions, thereby enabling the tubular guidewire assembly to function as a conventional guidewire for catheter exchanges.

7. The system of claim 1 further comprising means for selectively opening the extended sealable section distal to each successive permanent airtight seal to deflate the occlusive balloon.

8. The system of claim 1 wherein the gas is a biocompatible gas that will effectively go into solution in blood better than ambient air.

9. A guidewire occlusion system for use in vascular procedures comprising:
(a) a tubular guidewire assembly having an occlusive balloon proximate a distal end and an extended sealable section proximate a proximal end;
(b) a gas inflation/evacuation system removably connectible to the proximal end of the tubular guidewire assembly, including:
(1) an evacuation system that selectively evacuates the tubular guidewire assembly; and,
(2) an inflation system that selectively introduces a gas into the tubular guidewire assembly to inflate the occlusive balloon a plurality of times; and,
(c) a sealing system removably connectible to the proximal end of the tubular guidewire assembly that selectively seals the tubular guidewire assembly at one of a plurality of separate locations along the extended sealable section to form one of a plurality of successive permanent airtight seals of the tubular guidewire assembly along the extended sealable section to retain the gas in the occlusive balloon a plurality of times such that the occlusive balloon is capable of repeated inflation and deflation during a vascular procedure in between which the proximal end of the tubular guidewire assembly is free of mechanical connections and obstructions, thereby enabling the tubular guidewire assembly to function as a conventional guidewire for catheter exchanges.

10. The system of claim 9 wherein the tubular guidewire assembly has an effective length of at least 40 cm and an outer diameter of less than 0.060 inch, wherein the extended sealable section has an effective length of at least 1 cm and an outer diameter of less than 0.050 inch, and wherein the occlusive balloon can be deflated in less than two minutes.

11. The system of claim 9 wherein the tubular guidewire assembly has an effective length of at least 100 cm and an outer diameter of less than 0.018 inch, wherein the extended sealable section has an effective length of at least 5 cm and an outer diameter of less than 0.012 inch, and wherein the occlusive balloon can be deflated in less than one minute.

12. The system of claim 9 wherein the extended sealable section comprises a metallic tube and the sealing system comprises a crimping mechanism which permanently deforms and crimps a portion of the metallic tube closing the tube at the crimp.

13. The system of claim 12 wherein the metallic tube is dimensioned and the crimping mechanism is arranged such that an effective outer diameter of the metallic tube at the location of a seal is no greater than the outer diameter of a main body portion of the tubular guidewire assembly when the metallic tube is crimped at the location of the seal.

14. A guidewire occlusion system for use in vascular procedures comprising:
(a) a tubular guidewire assembly having an occlusive balloon along a distal end and an extended sealable section at a proximal end;
(b) a gas inflation system removably connectible to the proximal end of the tubular guidewire assembly capable of introducing a gas into the tubular guidewire assembly to inflate the occlusive balloon a plurality of times; and,
(c) a sealing system removably connectible to the proximal end of the tubular guidewire assembly, including:
(1) means for selectively sealing the tubular guidewire assembly at one of a plurality of separate locations along the extended sealable section to form one of a plurality of successive permanent airtight seals of the tubular guidewire assembly along the extended sealable section; and,
(2) means for severing the extended sealable section distal to each successive permanent airtight seal to release the gas from the occlusive balloon a plurality of times.

15. The system of claim 14 wherein the tubular guidewire assembly has an effective length of at least 100 cm and an outer diameter of less than 0.018 inch, wherein the extended sealable section has an effective length of at least 5 cm and an outer diameter of less than 0.012 inch, and wherein the occlusive balloon can be deflated in less than one minute.

16. The system of claim 14 wherein the means for selectively sealing comprises a crimping mechanism and the extended sealable section comprises an extended crimpable section.

17. The system of claim 16 wherein the extended crimpable section is dimensioned and the crimping mechanism is arranged such that an effective outer diameter of the extended crimpable section at the location of a seal is no greater than the outer diameter of a main body portion of the tubular guidewire assembly when the crimpable section is crimped at the location of the seal.

18. The system of claim 14 wherein the means for selectively sealing comprises a plugging mechanism that selectively inserts a plug of material into the proximal end of the extended sealable section while maintaining an airtight seal between the tubular guidewire assembly and the gas inflation system.

19. A guidewire occlusion system for use in vascular procedures comprising:
(a) a tubular guidewire assembly having an occlusive balloon proximate a distal end and an extended sealable section proximate a proximal end;
(b) an inflation system that selectively introduces a gas into the tubular guidewire assembly to inflate the occlusive balloon a plurality of times; and,
(c) a sealing system removably connectible to the proximal end of the tubular guidewire assembly that selectively seals the extended sealable section at one of a plurality of separate locations along the extended sealable section to form one of a plurality of successive permanent airtight seals of the tubular guidewire assembly along the extended sealable section to retain the gas in the occlusive balloon a plurality of times such that the occlusive balloon is capable of repeated inflation and deflation during a vascular procedure in between which the proximal end of the tubular guidewire assembly is free of mechanical connections and obstructions, thereby enabling the tubular guidewire assembly to function as a conventional guidewire for catheter exchanges.

20. The system of claim 19 wherein the tubular guidewire assembly has an effective length of at least 100 cm and an outer diameter of less than 0.018 inch, wherein the extended sealable section has an effective length of at least 5 cm and an outer diameter of less than 0.012 inch, and wherein the occlusive balloon can be deflated in less than one minute.

21. The system of claim 19 wherein the sealing system comprises a crimping mechanism and the extended sealable section comprises an extended crimpable section.

22. The system of claim 21 wherein the extended crimpable section is dimensioned and the crimping mechanism is arranged such that an effective outer diameter of the extended crimpable section at the location of a seal is no greater than the outer diameter of a main body portion of the tubular guidewire assembly when the extended crimpable section is crimped at the location of the seal.

23. A method for repeatedly occluding a blood vessel during a vascular procedure comprising:
(a) guiding a tubular guidewire assembly having an occlusive balloon proximate the distal end into a blood vessel and positioning the occlusive balloon distal to a region of the blood vessel to be treated;
(b) evacuating the occlusive balloon through the tubular guidewire assembly;
(c) introducing a biocompatible gas under pressure into the tubular guidewire assembly to inflate the occlusive balloon;
(d) sealing a proximal portion of the tubular guidewire assembly;
(e) introducing a catheter over a proximal end of the tubular guidewire assembly and over the sealed proximal portion of the tubular guidewire assembly and advancing the catheter over the tubular guidewire assembly to the region of the blood vessel to be treated;
(f) performing a procedure using the catheter as part of the procedure;
(g) removing the sealed portion of the tubular guidewire assembly thereby deflating the occlusive balloon; and,
(h) repeating at least steps (b)–(d) and (g) such that the occlusive balloon is inflated and deflated a plurality of times during the procedure.

24. The method of claim 23 wherein step (f) includes a step of aspirating at least a portion of the blood vessel prior to step (g).

25. The method of claim 23 wherein step (g) is performed within five minutes of step (c) and wherein step (g) is accomplished such that the occlusive balloon is substantially deflated and blood flow is reestablished in the blood vessel is less than two minutes.

26. The method of claim 25 wherein step (g) is accomplished such that the occlusive balloon is substantially deflated and blood flow is reestablished in the blood vessel in less than one minute.

27. A method for repeatedly occluding a blood vessel during a vascular procedure comprising:
(a) guiding a tubular guidewire assembly having an occlusive balloon proximate the distal end into a blood vessel and positioning the occlusive balloon distal to a region of the blood vessel to be treated;
(b) introducing a gas under pressure into the tubular guidewire assembly to inflate the occlusive balloon;
(c) sealing a proximal portion of the tubular guidewire assembly;
(d) introducing a catheter over a proximal end of the tubular guidewire assembly and over the sealed proximal portion of the tubular guidewire assembly and advancing the catheter over the tubular guidewire assembly to the region of the blood vessel to be treated;
(e) performing a procedure using the catheter as part of the procedure;
(f) removing the sealed portion of the tubular guidewire assembly thereby deflating the occlusive balloon; and,
(g) repeating at least steps (b)–(c) and (f) such that the occlusive balloon is inflated and deflated a plurality of times during the procedure.

28. The method of claim 27 wherein step (e) includes a step of aspirating at least a portion of the blood vessel prior to step (f).

29. The method of claim 27 wherein step (f) is performed within five minutes of step (b) and wherein step (f) is accomplished such that the occlusive balloon is substantially deflated and blood flow is reestablished in the blood vessel in less than two minutes.

30. The method of claim 29 wherein step (f) is accomplished such that the occlusive balloon is substantially deflated and blood flow is reestablished in the blood vessel in less than one minute.

31. The method of claim 27 wherein the procedure of step (e) is a thrombectomy procedure including the introduction and evacuation of a fluid from the region of the blood vessel to be treated such that the occlusive balloon when inflated prevents passage of the fluid downstream of the occlusive balloon.

32. A guidewire occlusion system for use in vascular procedures comprising:
(a) a tubular guidewire assembly having an occlusive balloon proximate a distal end and an extended sealable section proximate a proximal end;
(b) a gas inflation/evacuation system removably connectible to the proximal end of the tubular guidewire assembly, including:
(1) means for evacuating the tubular guidewire assembly; and,
(2) means for introducing a gas into the tubular guidewire assembly to inflate the occlusive balloon a plurality of times; and,
(c) a sealing system removably connectible to the proximal end of the tubular guidewire assembly which includes means for selectively sealing the tubular guidewire assembly by forming successive permanent airtight seals at separate locations along the extended sealable section to retain the gas in the occlusive balloon a plurality of times, the means for selectively sealing including a mechanism selected from the group of mechanisms consisting of a crimping mechanism and a plugging mechanism.

33. The system of claim 32 wherein the means for selectively sealing comprises a plugging mechanism that selectively inserts a plug of material into the distal end of the extended sealable section while maintaining an airtight seal between the tubular guidewire assembly and the gas inflation/evacuation system.

* * * * *

UNITED STATES PATENT AND TRADEMARK OFFICE
CERTIFICATE OF CORRECTION

PATENT NO. : 6,932,828 B2
DATED : August 23, 2005
INVENTOR(S) : Michael J. Bonnette and Eric J. Thor It is certified that error appears in the above-identified patent and that said Letters Patent is hereby corrected as shown below:

Title page,
Item [57], ABSTRACT,
Line 2, after "device" insert -- such as an occlusive balloon --;
Lines 5-6, "connectable" should be -- connectible --;
Line 6, "guidewire" should be -- tubular guidewire --;
Line 7, delete "air from";
Line 8, "guidewire" should be -- tubular guidewire assembly --;
Line 9, "guidewire" should be -- tubular guidewire assembly --;
Line 10, "balloon" should be -- devie --;
Line 11, "connectable" should be -- connectible --;
Line 11, "guidewire" should be -- tubular guidewire --;
Line 15, "guidewire" should be -- guidewire assembly --;
Line 16, after "desired" insert -- in order --.

Column 4,
Line 49, "connectable" should be -- connectible --.

Column 16,
Line 18, insert a new line -- 111 one-way check valve --;
Line 31, insert a new line -- 142 inflation manifold --;
Line 53, insert a new line -- 154 fingergrip --.

Signed and Sealed this

Thirtieth Day of May, 2006

JON W. DUDAS
*Director of the United States Patent and Trademark Office*